US012285259B2

(12) United States Patent
Zeidan et al.

(10) Patent No.: US 12,285,259 B2
(45) Date of Patent: *Apr. 29, 2025

(54) IDENTIFICATION AND VISUALIZATION OF CARDIAC ACTIVATION SEQUENCE IN MULTI-CHANNEL RECORDINGS

(71) Applicant: BIOSENSE WEBSTER (ISRAEL) LTD., Yokneam (IL)

(72) Inventors: Ziyad Zeidan, Zemmer (IL); Gal Hayam, Tivon (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/697,604

(22) Filed: Mar. 17, 2022

(65) Prior Publication Data

US 2022/0202335 A1 Jun. 30, 2022

Related U.S. Application Data

(63) Continuation of application No. 16/509,853, filed on Jul. 12, 2019, now Pat. No. 11,278,228, which is a
(Continued)

(51) Int. Cl.
*A61B 5/287* (2021.01)
*A61B 5/00* (2006.01)
(Continued)

(52) U.S. Cl.
CPC .............. *A61B 5/287* (2021.01); *A61B 5/061* (2013.01); *A61B 5/065* (2013.01); *A61B 5/316* (2021.01);
(Continued)

(58) Field of Classification Search
CPC ......... A61B 5/287; A61B 5/061; A61B 5/065; A61B 5/316; A61B 5/339; A61B 5/349;
(Continued)

(56) References Cited

U.S. PATENT DOCUMENTS 5,546,951 A 8/1996 Ben-Haim
5,637,090 A 6/1997 McGee et al.
(Continued)

FOREIGN PATENT DOCUMENTS

CN 1291903 A 4/2001
CN 101292870 A 10/2008
(Continued)

OTHER PUBLICATIONS

European Search Report dated Oct. 16, 2017 in corresponding European Patent Application No. 17175147.2.
(Continued)

*Primary Examiner* — Mallika D Fairchild
(74) *Attorney, Agent, or Firm* — Frost Brown Todd LLP (57) ABSTRACT

Intracardiac electrograms are recorded using a multi-electrode catheter and respective annotations established. Within a time window a pattern comprising a monotonically increasing local activation time sequence from a set of electrograms from neighboring electrodes is detected. The set is reordered and displayed for the operator.

20 Claims, 9 Drawing Sheets

Related U.S. Application Data continuation of application No. 15/179,002, filed on Jun. 10, 2016, now Pat. No. 10,349,855.

(51) Int. Cl.

| | |
|---|---|
| *A61B 5/06* | (2006.01) |
| *A61B 5/316* | (2021.01) |
| *A61B 5/339* | (2021.01) |
| *A61B 5/349* | (2021.01) |
| *A61B 5/352* | (2021.01) |
| *A61B 5/361* | (2021.01) |

(52) U.S. Cl.
CPC .............. *A61B 5/339* (2021.01); *A61B 5/349* (2021.01); *A61B 5/352* (2021.01); *A61B 5/361* (2021.01); *A61B 5/6858* (2013.01); *A61B 5/7264* (2013.01)

(58) Field of Classification Search
CPC ....... A61B 5/352; A61B 5/361; A61B 5/6858; A61B 5/7264; A61B 5/335; A61B 5/6852; A61B 5/6869; A61B 5/318
See application file for complete search history.

(56) References Cited

U.S. PATENT DOCUMENTS

| | | | |
|---|---|---|---|
| 5,738,096 | A | 4/1998 | Ben-Haim |
| 6,226,542 | B1 | 5/2001 | Reisfeld |
| 6,236,883 | B1 | 5/2001 | Ciaccio et al. |
| 6,301,496 | B1 | 10/2001 | Reisfeld |
| 6,690,963 | B2 | 2/2004 | Ben-Haim et al. |
| 6,814,733 | B2 | 11/2004 | Schwartz et al. |
| 6,892,091 | B1 | 5/2005 | Ben-Haim et al. |
| 6,997,924 | B2 | 2/2006 | Schwartz et al. |
| 7,156,816 | B2 | 1/2007 | Schwartz et al. |
| 7,435,221 | B1 | 10/2008 | Bharmi et al. |
| 7,536,218 | B2 | 5/2009 | Govari et al. |
| 7,756,576 | B2 | 7/2010 | Levin |
| 7,841,986 | B2 | 11/2010 | He et al. |
| 8,326,419 | B2 | 12/2012 | Rosenburg et al. |
| 8,577,450 | B1 | 5/2013 | Chmiel et al. |
| 8,478,383 | B2 | 7/2013 | Bar-Tal |
| 8,768,440 | B1 | 7/2014 | Brodnick et al. |
| 9,002,442 | B2 | 4/2015 | Harley et al. |
| 10,349,855 | B2 | 7/2019 | Zeidan et al. |
| 11,278,228 | B2 | 3/2022 | Zeidan et al. |
| 2007/0232949 | A1 | 10/2007 | Saksena |
| 2011/0251505 | A1 | 10/2011 | Narayan et al. |
| 2012/0089038 | A1 | 4/2012 | Ryu et al. |
| 2012/0284003 | A1 | 11/2012 | Gosh et al. |
| 2013/0006131 | A1 | 1/2013 | Narayan et al. |
| 2013/0079650 | A1 | 3/2013 | Turgeman |
| 2014/0005562 | A1 | 1/2014 | Bunch et al. |
| 2014/0052013 | A1 | 2/2014 | Narayan et al. |
| 2014/0066787 | A1 | 3/2014 | Narayan et al. |
| 2014/0081114 | A1 | 3/2014 | Shachar et al. |
| 2014/0172804 | A1 | 6/2014 | Kaufmann et al. |
| 2014/0180051 | A1 | 6/2014 | Thakur et al. |
| 2014/0288451 | A1 | 9/2014 | Brodnick et al. |
| 2014/0303469 | A1 | 10/2014 | Kordis et al. |
| 2015/0196216 | A1 | 7/2015 | Laughner et al. |
| 2015/0208938 | A1 | 7/2015 | Houben et al. |
| 2015/0208942 | A1 | 7/2015 | Bar-Tal et al. |
| 2015/0216438 | A1 | 8/2015 | Bokan et al. |
| 2016/0073913 | A1* | 3/2016 | Francis .................. A61B 5/743 600/512 |

FOREIGN PATENT DOCUMENTS

| | | |
|---|---|---|
| CN | 101558993 A | 10/2009 |
| CN | 102337262 A | 2/2012 |
| CN | 103354730 A | 10/2013 |
| CN | 103892824 A | 7/2014 |
| CN | 104414748 A | 3/2015 |
| JP | 2015-054250 A | 3/2015 |
| JP | 2016-039901 A | 3/2016 |
| WO | WO 1996/05768 A1 | 2/1996 |
| WO | 2015/130824 A1 | 9/2015 |

OTHER PUBLICATIONS

Chinese Office Action, First Office Action and First Search, dated Apr. 14, 2021 for Application No. CN 201710436390.0, 10 pgs.
Chinese Office Action, The Second Office Action and Supplementary Search, dated Sep. 16, 2021 for Application No. CN 201710436390.0, 11 pgs.
European Search Report and Written Opinion dated Oct. 16, 2017 for Application No. EP 17175147.2, 8 pgs.
European Examination Report dated Feb. 25, 2019 for Application No. EP 17175147.2, 5 pgs.
Japanese Office Action, Notice of Reasons for Refusal and Search Report by Registered Search Organization, dated Mar. 16, 2021 for Application No. JP 2017-114075, 16 pgs.
Gou, Wei & Lin Yang, "Comprehensive Understanding of the Electrophysiological Basis of Early Cardiac Afterdepolarization," Chinese Journal of Cardiac Pacing and Electrophysiology, vol. 28, Issue No. 5, Dec. 31, 2014, pp. 379-383.
Rottmann, M., et al., "Local activation time based estimation of the direction of propagation of plane wave and the corresponding conduction velocity in simulated electrograms," Biomedical Engineering, 59, Oct. 31, 2014, S136-+.
Yuemei, Hou "Current Status of Clinical Cardiac Electrophysiological Mapping Technology and Its Application", Chinese Journal of Cardiac Pacing and Electrophysiology, Issue No. 1, Dec. 31, 2004, pp. 379-383.
Zhang Zhongquan, Luo Lin, *Family Medication Instructions*, Inner Mongolia Science and Technology Press, Jul. 31, 2003) vol. 4.

* cited by examiner

IDENTIFICATION AND VISUALIZATION OF CARDIAC ACTIVATION SEQUENCE IN MULTI-CHANNEL RECORDINGS

CROSS-REFERENCE TO RELATED APPLICATION(S)

This application is a continuation of U.S. patent application Ser. No. 16/509,853, filed Jul. 12, 2019, now U.S. Pat. No. 11,278,228, which is a continuation of U.S. patent application Ser. No. 15/179,002, filed Jun. 10, 2016, now U.S. Pat. No. 10,349,855, the entire content of each of which is incorporated herein by reference.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to cardiac physiology. More particularly, this invention relates to the evaluation of electrical propagation in the heart.

2. Description of the Related Art

The meanings of certain acronyms and abbreviations used herein are given in Table 1.

TABLE 1

| Acronyms and Abbreviations | |
| --- | --- |
| ECG | Electrocardiogram |
| LAT | Local Activation Time |
| CPM | Current Position Map |
| RAP | Repetitive Activation Pattern |

Cardiac arrhythmias such as atrial fibrillation are an important cause of morbidity and death. Commonly assigned U.S. Pat. Nos. 5,546,951, 6,690,963, both issued to Ben Haim and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. Nos. 6,226,542, and 6,301,496, both issued to Reisfeld, which are incorporated herein by reference. As indicated in these patents, location and electrical activity is typically initially measured on about 10 to about 20 points on generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein in its entirety by reference, maps depicting such motion characteristics may be constructed when the trajectory information is sampled at a sufficient number of points in the heart.

Electrical activity at a point in the heart is typically measured by advancing a multiple-electrode catheter to measure electrical activity at multiple points in the heart chamber simultaneously. A record derived from time varying electrical potentials as measured by one or more electrodes is known as an electrogram. Electrograms may be measured by unipolar or bipolar leads, and are used, e.g., to determine onset of electrical propagation at a point, known as local activation time.

However, determination of local activation time as an indicator of electrical propagation becomes problematic in the presence of conduction abnormalities. For example, atrial electrograms during sustained atrial fibrillation have three distinct patterns: single potential, double potential and complex fractionated atrial electrograms. Thus, compared to a normal sinus rhythm signal, an atrial fibrillation signal is extremely complex, as well as being more variable. While there is noise on both types of signal, which makes analysis of them difficult, because of the complexity and variability of the atrial fibrillation signal the analysis is correspondingly more difficult. On the other hand, in order to overcome the atrial fibrillation in a medical procedure, it is useful to establish possible paths of activation waves travelling through the heart representing atrial fibrillation. Once these paths have been identified, they may be blocked, for example, by appropriate ablation of a region of the heart. The paths may be determined by analysis of intra-cardiac atrial fibrillation signals, and embodiments of the present invention facilitate the analysis.

SUMMARY OF THE INVENTION

A typical multi-electrode catheter, such as the Pentaray® NAV catheter, has on its distal end numerous electrodes (approximately 60 or more), which acquire respective sets of ECG signals from different points in the heart. These electrodes are distributed over the splines. The signals may be presented as individual graphs of time-varying signal voltages. Conventionally, the order of presentation of these graphs is according to the electrode position on the splines. In such displays of multielectrode catheter recordings, it is difficult to follow the activation sequence in different electrodes. Therefore it is not easy to identify the existence of reentrant activation pathways or their location.

Embodiments of the present invention simultaneously acquire electropotential signals in the heart using a catheter having a multiplicity of electrodes at its distal end, each electrode generating a respective unipolar signal. The signals may be considered as unipolar signals, or in combination with another electrode, as bipolar signals. Each of the ECG signals are annotated to find the local activation time (LAT) and displayed as time-varying voltages. The graphs are then further analyzed to detect relationships in the LATs obtained from neighboring points in the heart, for example a monotonic increase in LAT. If a pattern is found, the graphs are reordered to include a new group whose members present the pattern. By analyzing the reordered graphs over time, mutations in conduction patterns at neighboring locations can conveniently be detected.

There is provided according to embodiments of the invention a method which is carried out by inserting a multielectrode probe into a heart of a living subject, recording respective intracardiac electrograms from the electrodes, establishing respective annotations for the electrograms, and within a time window detecting from the annotations a velocity pattern comprising a monotonically increasing local activation time sequence in a set of the electrograms and the electrodes thereof, wherein each electrode of the set is disposed within a predetermined distance from at least one other electrode of the set, and displaying the electrograms of the set.

According to another aspect of the method, the electrograms are recorded concurrently.

A further aspect of the method includes sorting the set according to positions on the probe of the electrodes thereof.

According to yet another aspect of the method, the pattern can be a reentrant activation circuit, a micro reentry pattern, a focal source pattern, and a macro reentry pattern.

According to one aspect of the method, displaying the electrograms of the set includes sorting the set according to local activation times thereof.

Still another aspect of the method is carried out in a new time window by detecting a change in the pattern, and responsively to the change, iterating sorting the set and displaying the electrograms.

According to an additional aspect of the method, the change includes a change in a direction of electrical propagation.

According to one aspect of the method, the change includes a change in a speed of electrical propagation.

There is further provided according to embodiments of the invention an apparatus including a probe having a plurality of electrodes on a distal portion thereof, electrical circuitry for recording respective time-varying electrograms from the electrodes when the probe is at a location in a heart of a living subject, a memory for storing the electrograms, a display, and a processor connected to the memory. The processor is operative for establishing annotations of local activation times from the respective intracardiac electrograms, defining a pattern from the annotations that includes a velocity of electrical propagation in the heart, within a time window detecting a monotonically increasing local activation time sequence pattern in the annotations of a set of the electrograms and the electrodes thereof, each electrode of the set being disposed within a predetermined distance from at least one other electrode of the set, and displaying the electrograms of the set on the display.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Definitions

Annotations" or "annotation points" refer to points or candidates on an electrogram that are considered to denote events of interest. In this disclosure the events are typically onset (local activation time) of the propagation of an electrical wave as sensed by the electrode.

For purposes of this disclosure two electrodes are proximate or "close to" each other, when either they are within 15 mm of one another on the catheter, or they are nearest to one another among other electrodes in space or in position on the catheter, e.g., succeeding one another in position on a ray of a spline catheter or a spine of a basket catheter. Two electrodes may also be "close to" one another if they are on corresponding or succeeding positions of two spines or rays that are not separated by intervening spines or rays.

Overview

Figure 1:
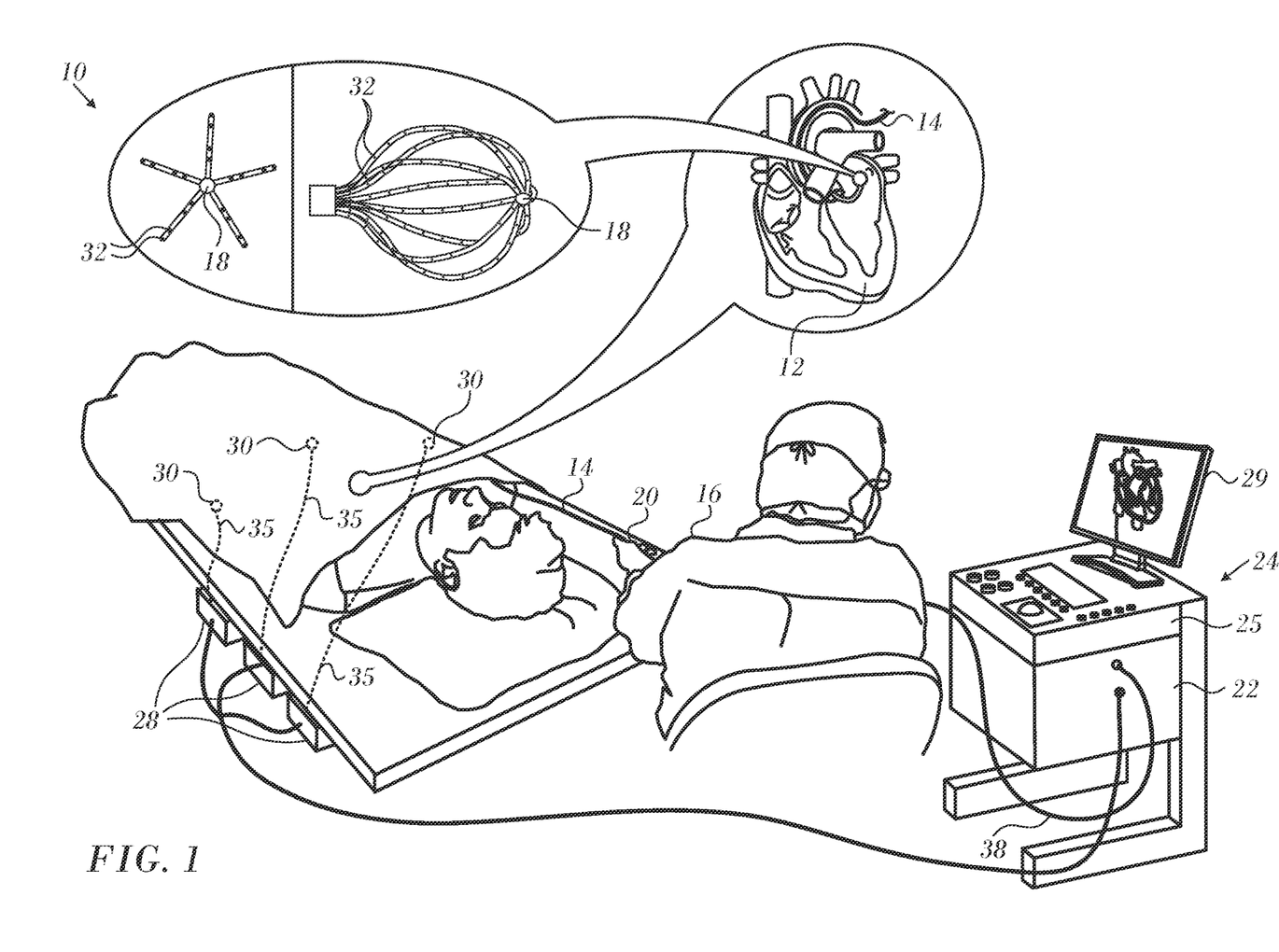
FIG. 1 is a pictorial illustration of a system for evaluating electrical activity in a heart of a living subject in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic. One commercial product embodying elements of the system 10 is available as the CARTO® 3 System, available from Biosense Webster, Inc., 3333 Diamond Canyon Road, Diamond Bar, CA 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

The catheter 14 is a multi-electrode catheter, which can be a basket catheter as shown in the right portion of the balloon or a spline catheter as shown in the left portion. In any case there are multiple electrodes 32, which are used as sensing electrodes and have known locations on the basket or spline, and known relationships to one another. Thus, once the catheter is located in the heart, for example by constructing a current position map, the location of each of the electrodes 32 in the heart is known. One method for generation of a current position map is described in commonly assigned U.S. Pat. No. 8,478,383 to Bar-Tal et al., which is herein incorporated by reference.

Electrical signals can be conveyed to and from the heart 12 from the electrodes 32 located at or near the distal tip 18 of the catheter 14 via cable 34 to the console 24. Pacing signals and other control signals may be conveyed from the console 24 through the cable 34 and the electrodes 32 to the heart 12.

Wire connections 35 link the console 24 with body surface electrodes 30 and other components of a positioning sub-system for measuring location and orientation coordinates of the catheter 14. The processor 22, or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted near the distal tip 18 of the catheter 14.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes as described in further detail below.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. The system 10 may receive image data from an external imaging modality, such as an MRI unit or the like and includes image processors that can be incorporated in or invoked by the processor 22 for generating and displaying images that are described below.

Figure 2:
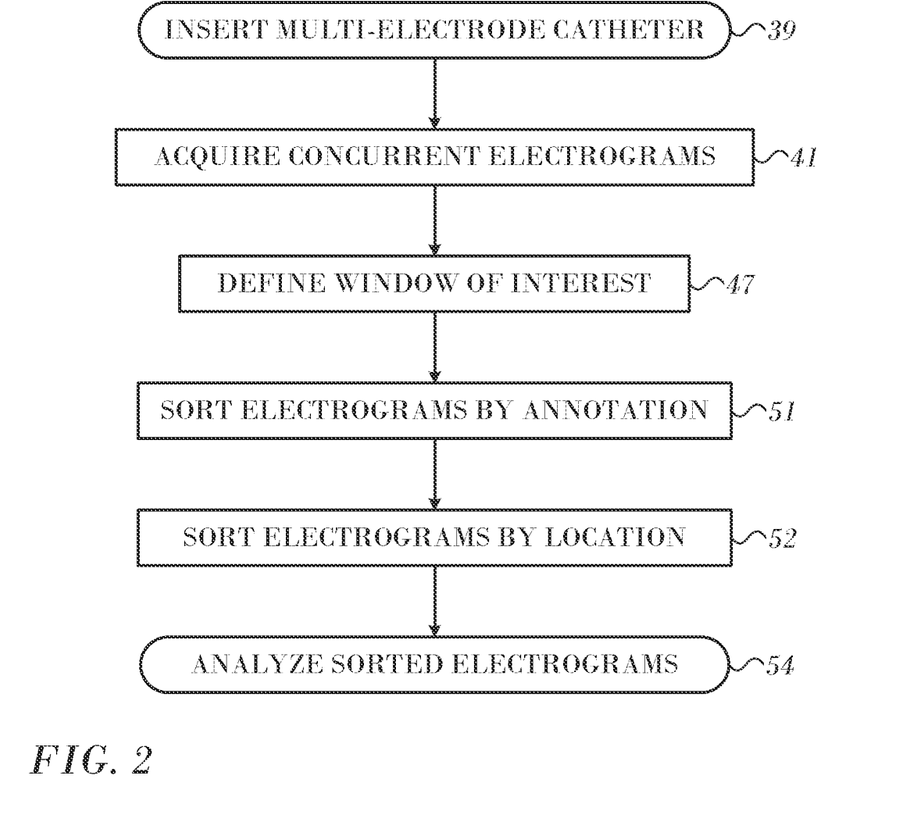
FIG. 2 is a flow chart of a method for processing multichannel electrical recordings of the heart in accordance with an embodiment of the invention.

Reference is now made to FIG. 2, which is a flow chart of a method for processing multi-channel electrical recordings of the heart in accordance with an embodiment of the invention. The process steps are shown in a particular linear sequence in FIG. 1 and other flow charts herein for clarity of presentation. However, it will be evident that many of the steps can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At initial step 39 a chamber of the heart is catheterized conventionally with a multi-electrode catheter. Either a multi-spline catheter of a basket catheter is suitable. In such catheters each electrode has a known position on the basket or the splines as the case may be. Once the catheter is in place, if desired a current position map may be constructed using location sensors in the catheter, for example magnetic location sensors or using impedance measurements as noted above. The location of each of the electrodes in the heart is known from the current position map, or can be determined using imaging techniques. A typical multi-spline catheter used with the CARTO 3 system has, on its distal end, 60 electrodes, which acquire 60 sets of ECG signals from 60 points in the heart. The electrodes are distributed over the splines, assumed herein to be eight splines. The signals may be presented as 60 voltage vs time graphs. The order of presentation of the 60 graphs is typically according to the electrode position on the splines. While exemplified by the discussion of FIG. 2, other suitable catheters may have relatively more or fewer electrodes.

Next, at step 41 intracardiac electrograms are recorded concurrently from of the electrodes in respective channels. The recordings are annotated, for example by determining time windows in which there is a maximal change in voltage, i.e., a maximum value of |dv/dt|. In cases of conduction abnormalities where electrical propagation is more complex, annotation may be accomplished using the teachings of commonly assigned U.S. Patent Application Publication No. 20150208942, entitled *Double Bipolar Configuration for Atrial Fibrillation Annotation* by Bar-Tal et al., whose disclosure is herein incorporated by reference.

Figure 3:
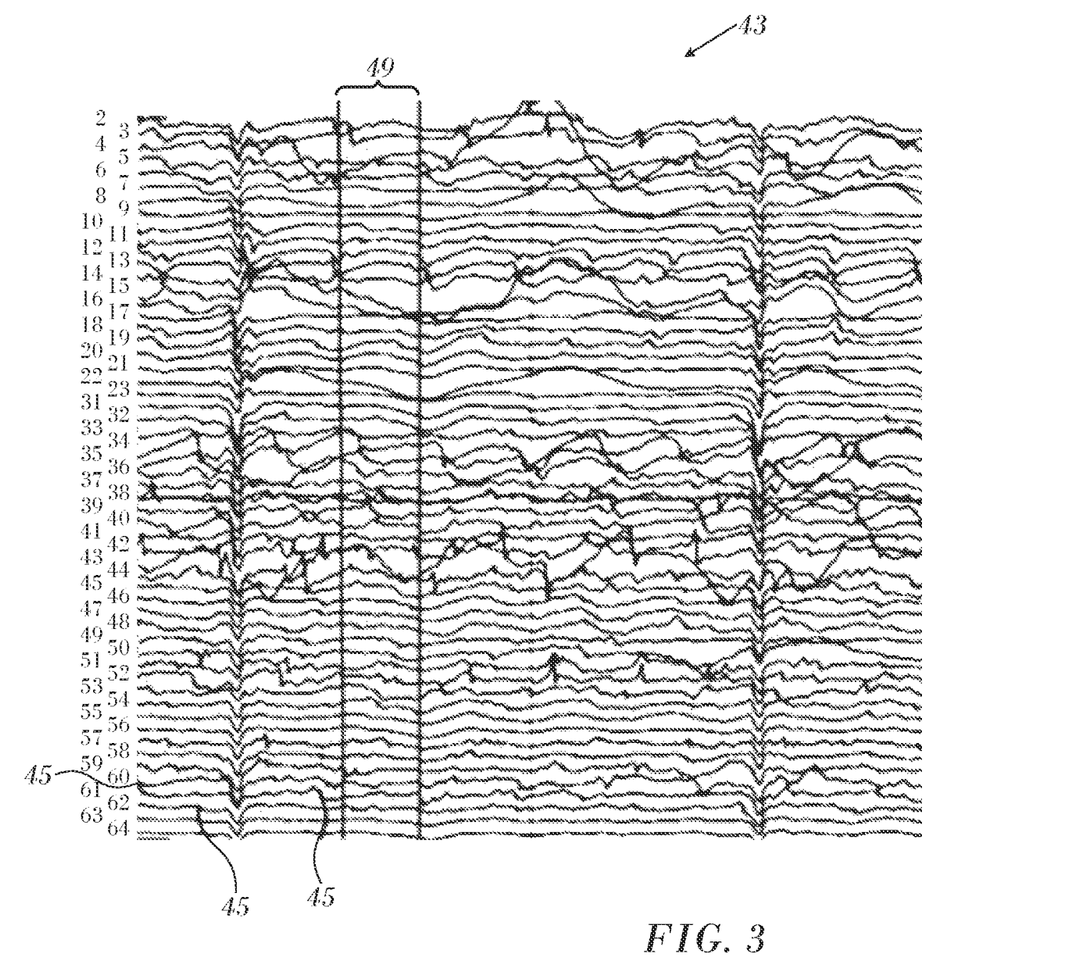
FIG. 3 is a presentation of a group of electrograms in accordance with an embodiment of the invention.

In order to better illustrate the difficulties that can be solved by application of the principles of the invention, reference is now made to FIG. 3, which is a presentation of a group of electrograms 43 the order of which is initially available after completion of step 41, and modified in accordance with the principles of the invention. The electrograms were recorded for at least a complete cardiac cycle, and annotated by performing step 41. Annotations 45 in the electrograms are indicated representatively. The electrograms are numbered 2-64, corresponding to readings from unipolar electrodes that are identified using an arbitrary positioning scheme on the catheter. It is evident that a variety of patterns are present without any order that would be convenient for a human observer. Thus, in the abnormal electrograms shown in FIG. 3 relationships among the tracings are not visually evident.

Continuing to refer to FIG. 2 and FIG. 3, at step 47 a complete cardiac cycle is identified in the group of electrograms 43, for example by reference to a standard ECG. Alternatively, step 47 can be performed automatically be done by detecting the R-wave and differentiating the R-wave detection times as taught in commonly assigned U.S. Patent Application Publication No. 20150208938, entitled *Hybrid Bipolar/Unipolar Detection of Activation Wavefront*, which is herein incorporated by reference. When differentiation is applied to an electrogram, the data series generated indicates a change in voltage (per unit time) rather than the absolute voltage. Therefore, the differentiated electrogram represents the slope of the raw electrogram at any given time point. Further alternatively, other characteristics of an electrogram may be used to define cardiac cycles, as is known in the art. In FIG. 3 a cardiac cycle is represented as a window of interest 49.

Figure 5:
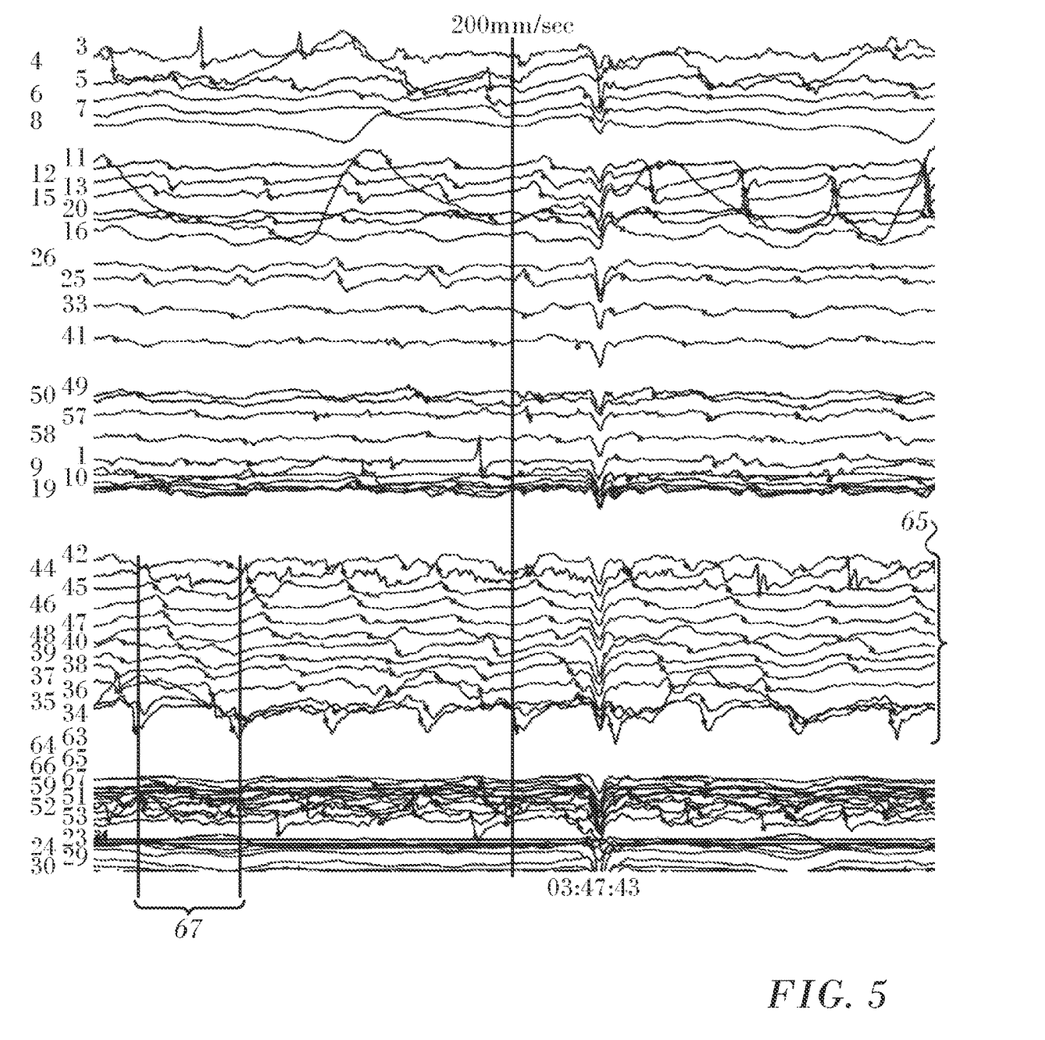
FIG. 5 is a screen display in which electrograms have been grouped according to a grouping algorithm in accordance with an embodiment of the invention.

In FIG. 2, next, at step 51 the electrograms are automatically sorted according to their annotated activation times. An example is shown in FIG. 5.

Next, in step 52 the groups of electrograms are sorted again, now according to location of the electrodes. Sorting can be done according to location of electrodes on the catheter, first along the spline and then between adjacent splines. Alternatively, electrodes may be grouped according to location in the heart and the groups sorted by proximity.

Figure 4:
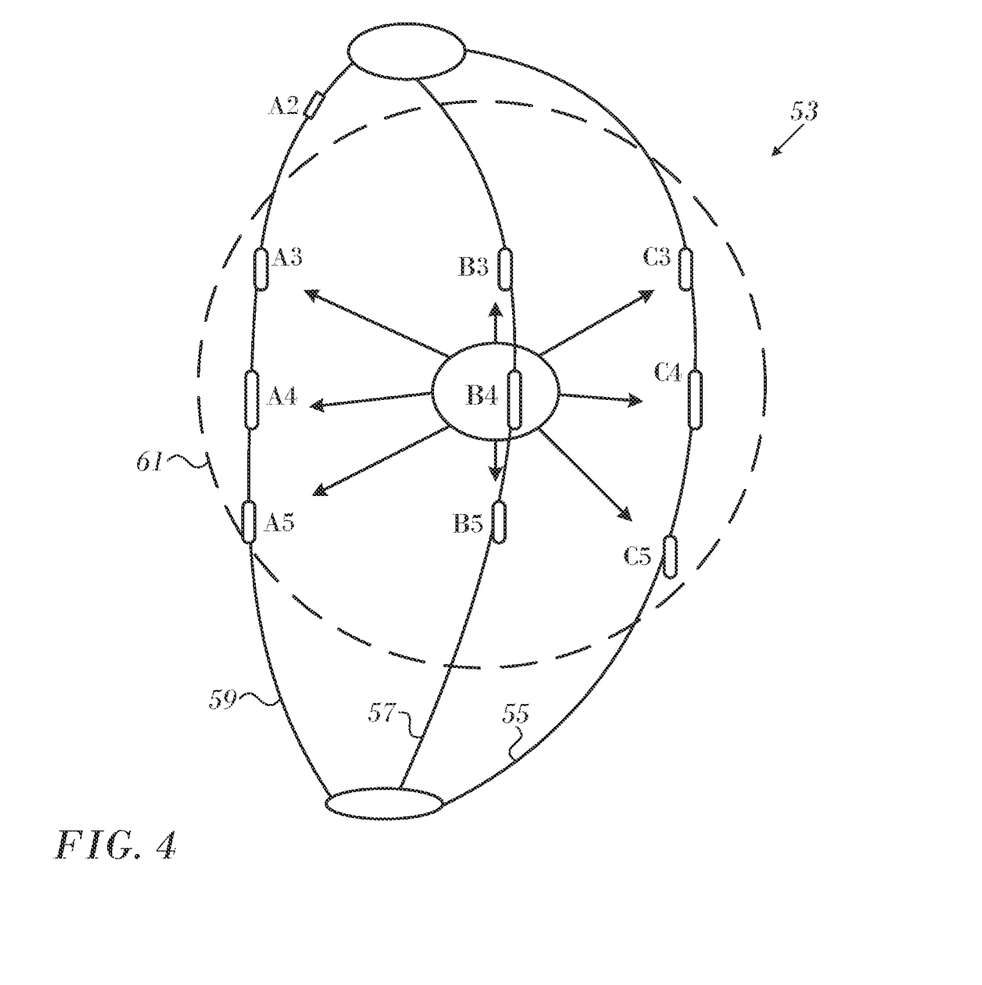
FIG. 4 is a schematic diagram that explains the notion of proximity of electrodes to one another on a multielectrode catheter in accordance with an embodiment of the invention.

Reference is now made to FIG. 4, which is a schematic diagram that explains the notion of proximity of electrodes to one another on a multielectrode catheter in accordance with an embodiment of the invention. A basket catheter 53 has a plurality of electrodes disposed on its spines Listing 55, 57, 59. All of electrodes A3-A5, B3, B5, and C3-C5 lie within a predetermined distance from electrode B4, demarcated by a circle 61, which is a 2-dimensional projection of a sphere, and are "close to" electrode B4. Electrode A2 lies outside the circle 61 and is farther from electrode B4 than the predetermined distance. Electrode A2 is not close to electrode B4.

The benefits of sorting groups of electrograms are described below with reference to FIG. 6-FIG. 9, all having the same formats, in which numbers identifying the electrograms on the right correspond to numbered locations in the left pane.

Returning to FIG. 2, in final step 54 an analysis is performed on the sorted electrograms. This may be done automatically or with operator assistance. In any case, the rearrangement of the electrograms enables the operator to quickly appreciate conduction velocity patterns comprising speed and direction of electrical propagation of interest for purposes of diagnosis and consideration for ablation. The method provides a visual indication of the existence of a variety of conduction or activation patterns, e.g., reentry cycles, multiple dispersed pathways. Furthermore, the method produces a visual indication whether the activation pattern covers the entire duration of the cardiac cycle or only a portion of it. It enables identification and localization of local reentrant activation circuits, such as rotors in atrial fibrillation, micro reentry, focal source, and macro reentry patterns.

Reference is now made to FIG. 5, which is a screen display in which the electrograms have been grouped according to a grouping algorithm in accordance with an embodiment of the invention. One algorithm searches for sequences of electrograms taken from points that are close to one another, and which exhibit a monotonic increase in LAT, referred to herein as a local activation time sequence pattern. When such a sequence is found, the electrographs are associated in an order of increasing LAT, for example group 65. If such a pattern is found, the graphs are re-ordered in order of the LAT to display the pattern, for example as shown by window 67.

Figure 6:
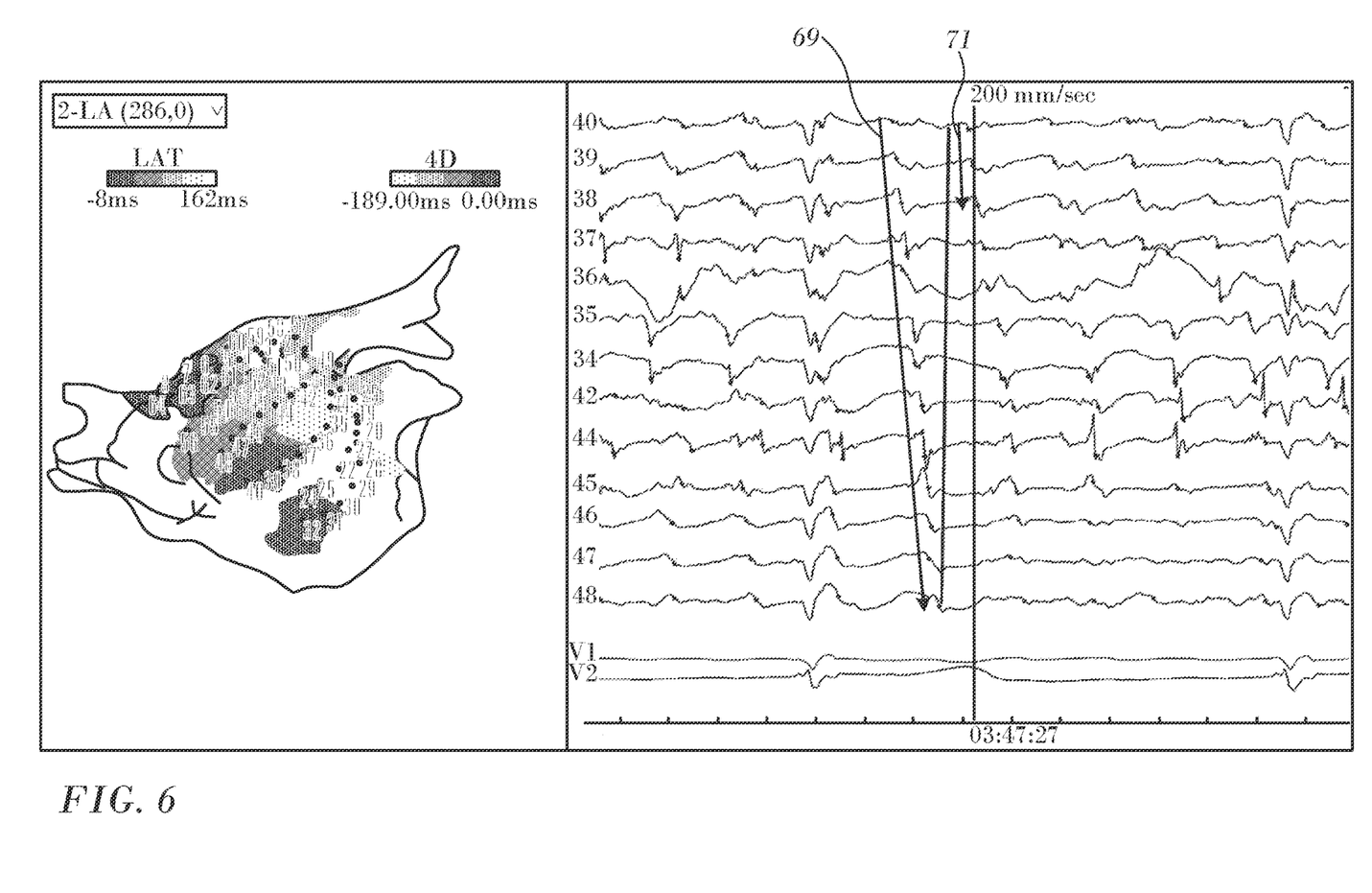
FIG. 6 is a screen display in which the electrograms have been grouped according to a grouping algorithm and sorted by location in accordance with an embodiment of the invention.

Reference is now made to FIG. 6, in which the sort by electrogram locations has identified a rotational repetitive activation pattern (RAP), indicated by lines 69, 71.

Figure 7:
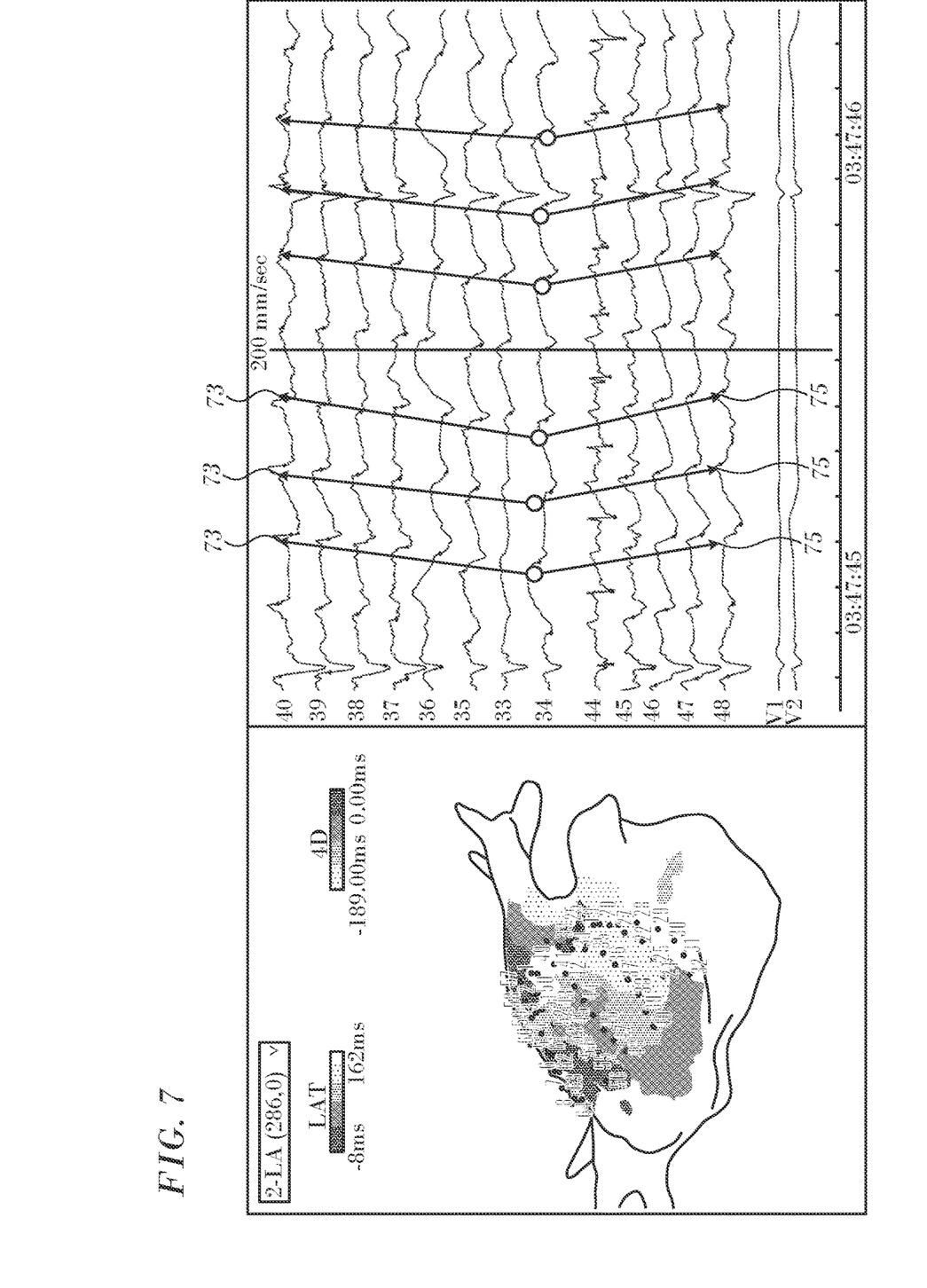
FIG. 7 is a screen display in which the electrograms were made from a spline catheter, grouped according to a grouping algorithm and sorted in accordance with an embodiment of the invention.

Another effect of ordering the electrograms by location is shown in FIG. 7, in which electrograms were obtained with spline catheter. Propagation detected along a first spline is indicated by upward directed arrows 73, and along a second spline by downward directed arrows 75. FIG. 7 demonstrates a focal activation profile.

Figure 8:
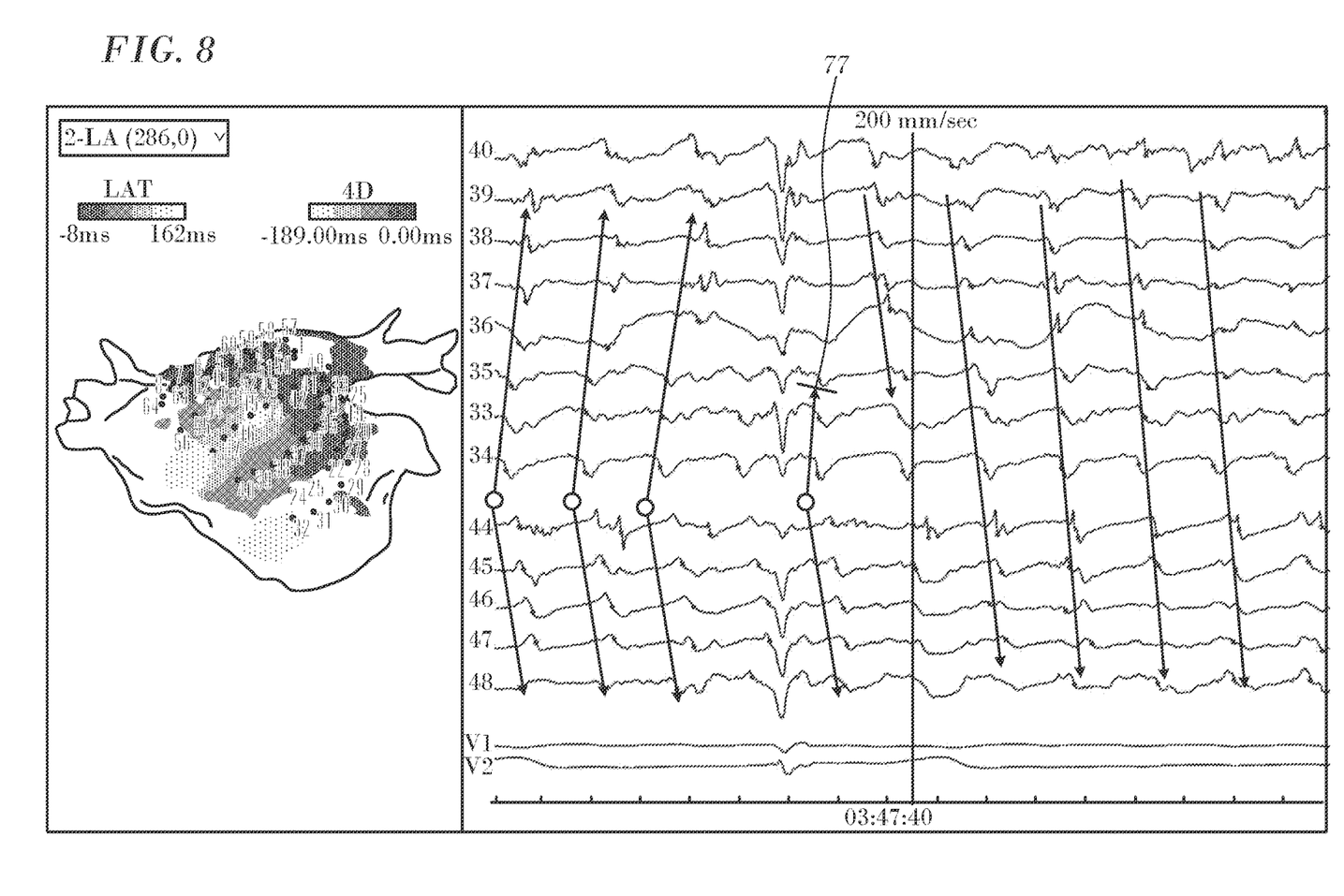
FIG. 8 is a screen display in which the electrograms have been grouped according to a grouping algorithm and sorted by location in accordance with an embodiment of the invention.
Figure 9:
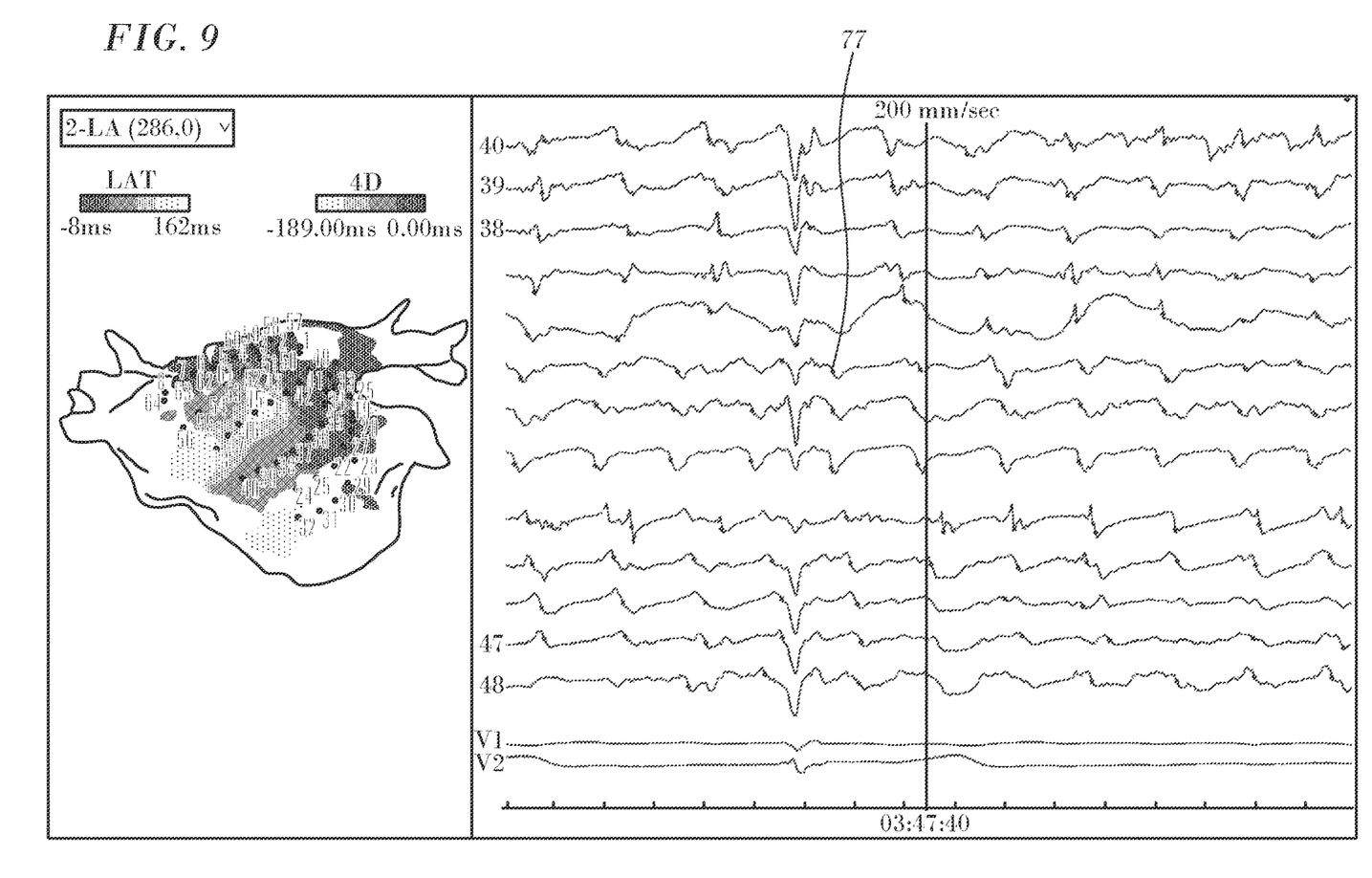
FIG. 9 is a modification of FIG. 8 in which activation lines transition are deleted.

Another pattern revealed by ordering the electrograms by location is shown in FIG. 8. A transition is shown at point 77 in electrode No. 35 from a focal repetitive activation pattern (RAP), representing focal electrical activity, to a rotational repetitive activation pattern, representing reentrant activity. FIG. 9 is a modified version of FIG. 8, in which the activation lines during the transition are deleted. Point 77 now indicates the establishment of the new activation pattern.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

What is claimed is:

1. A method comprising:
   inserting a probe into a heart of a living subject, the probe having a plurality electrodes;
   recording respective electrograms from the electrodes;
   establishing annotations for each of the electrograms, including annotated activation times;
   representing a complete cardiac cycle identified in the electrograms as a time window of interest;
   sorting the electrograms by the annotated activation times;
   resorting the electrograms in groups according to:
   (i) a proximity of the electrodes to each other on the probe, the proximity being defined by a predetermined distance between the electrodes;
   (ii) monotonic increase in the annotation activation times; and
   (iii) an order of increasing annotation activation times;
   displaying the electrograms in a graph of time-varying signal voltages, as resorted into the groups wherein all electrodes of a group are located within the predetermined distance of a selected electrode so as to reveal a repetitive activation pattern within the complete cardiac cycle that is visible to a human observer; and
   ablating a region of the heart based on the graph.

2. The method of claim 1, wherein displaying the electrograms includes displaying a visual indication that includes an arrow indicative of a direction of propagation.

3. The method of claim 2, wherein the visual indication includes upward directed and downward directed arrows.

4. The method of claim 2, wherein the direction of propagation includes a direction of propagation of a focal activation profile.

5. The method of claim 2, wherein the sorting the electrograms includes re-ordering the electrograms in order of the annotated activation times.

6. The method of claim 1, wherein displaying the electrograms includes displaying a visual indication that includes a transition point.

7. The method of claim 6, wherein the transition point includes a transition point of a focal repetitive activation pattern to a rotational repetitive activation pattern.

8. The method of claim 1, wherein sorting the electrograms includes sorting electrograms taken from points in the heart that are within a predetermined distance and exhibit a monotonic increase in annotated activation times.

9. The method of claim 1, wherein the predetermined distance is within 15 mm.

10. The method of claim 1, wherein the electrograms are recorded concurrently.

11. An apparatus comprising:
    a probe configured for insertion into a heart, the probe having a plurality electrodes;
    electrical circuitry for recording respective electrograms from the electrodes;
    a memory for storing the electrograms;
    a display; and
    a processor connected to the memory and operative to:
    record respective electrograms from the electrodes;
    establish annotations for each of the electrograms, including annotated activation times, the annotations being based on a change in voltage per unit time and defining a pattern of electrical propagation in the heart;
    represent a complete cardiac cycle identified in the electrograms as a time window of interest;
    sort the electrograms by the annotated activation times;
    resort the electrograms in groups according to:
    (i) a proximity of the electrodes to each other on the probe, the proximity being defined by a predetermined distance between the electrodes
    (ii) monotonic increase in the annotation activation times; and
    (iii) an order of increasing annotation activation times;
    display the electrograms in a graph of time-varying signal voltages, as resorted into the groups wherein all electrodes of a group are located within the predetermined distance of a selected electrode so as to reveal a repetitive activation pattern visible to a human observer; and
    activate the probe to ablate a region of the heart based on the graph.

12. The apparatus of claim 11, wherein the processor is operative to display a visual indication on the display that includes an arrow indicative of a direction of propagation.

13. The apparatus of claim 12, wherein the visual indication includes upward directed and downward directed arrows.

14. The apparatus of claim 12, wherein the direction of propagation includes a direction of propagation of a focal activation profile.

15. The apparatus of claim 11, wherein the processor is operative to display a visual indication on the display that includes a transition point.

16. The apparatus of claim 15, wherein the transition point includes a transition point of a focal repetitive activation pattern to a rotational repetitive activation pattern.

17. The apparatus of claim 11, wherein the processor is operative to sort the electrograms taken from points in the heart that are within a predetermined distance and exhibit a monotonic increase in annotated activation times.

18. The apparatus of claim 11, wherein the predetermined distance is within 15 mm.

19. The apparatus of claim 11, wherein the processor is operative to sort the electrograms by re-ordering the electrograms in order of the annotated activation times.

20. The apparatus of claim 11, wherein the electrograms are recorded concurrently.

* * * * *